(12) United States Patent
Hartkens et al.

(10) Patent No.: US 9,629,710 B2
(45) Date of Patent: Apr. 25, 2017

(54) INTRAOCULAR LENS HAVING AN OPTICAL AND A HAPTIC PART, METHOD FOR MAKING AN INTRAOCULAR LENS AND METHOD FOR IMPLANTING AN INTRAOCULAR LENS INTO AN EYE

(71) Applicant: Carl Zeiss Meditec AG, Jena (DE)

(72) Inventors: Thomas Hartkens, Berlin (DE); Marco Wilzbach, Stuttgart (DE); Michael Stefan Rill, Jena (DE); Frederik Siegmann, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/664,514

(22) Filed: Mar. 20, 2015

(65) Prior Publication Data

US 2015/0265398 A1  Sep. 24, 2015

Related U.S. Application Data

(60) Provisional application No. 61/968,739, filed on Mar. 21, 2014.

(51) Int. Cl.
*A61F 2/16* (2006.01)
*A61F 2/14* (2006.01)
*A61F 9/008* (2006.01)

(52) U.S. Cl.
CPC ............... *A61F 2/16* (2013.01); *A61F 9/008* (2013.01); *A61F 9/00821* (2013.01); *A61F 2002/16901* (2015.04); *A61F 2220/0008* (2013.01)

(58) Field of Classification Search
CPC .. A61F 9/00821; A61F 9/008; A61F 9/00812; A61F 9/00834; A61F 2/16; A61F 2002/1681; A61F 2002/16901; A61F 2002/16903; A61F 2002/169
See application file for complete search history.

(56) References Cited

U.S. PATENT DOCUMENTS 6,322,589 B1 * 11/2001 Cumming ............... A61F 2/16
                                                          623/6.43
8,241,355 B2 *  8/2012 Brady ................... A61F 2/1635
                                                          623/6.37

OTHER PUBLICATIONS

STIC search results.*

* cited by examiner

*Primary Examiner* — David Isabella
*Assistant Examiner* — Dinah Baria
(74) *Attorney, Agent, or Firm* — Walter Ottesen, P.A.

(57) ABSTRACT

An intraocular lens has an optical part and a haptic adjoining the optical part. At least one additional fixation element that differs from the haptic is formed on at least an upper side of the intraocular lens. The additional fixation element is formed to fix the position of the intraocular lens in the capsular bag of an eye. A method for making an intraocular lens and a method for implanting an intraocular lens in a capsular bag of an eye are also disclosed.

6 Claims, 3 Drawing Sheets

INTRAOCULAR LENS HAVING AN OPTICAL AND A HAPTIC PART, METHOD FOR MAKING AN INTRAOCULAR LENS AND METHOD FOR IMPLANTING AN INTRAOCULAR LENS INTO AN EYE

CROSS REFERENCE TO RELATED APPLICATION

This application claims priority of U.S. provisional patent application Ser. No. 61/968,739, filed Mar. 21, 2014, the entire content of which is incorporated herein by reference.

FIELD OF THE INVENTION

The invention relates to an intraocular lens having an optical part and a haptic adjoining the optical part and arranged thereon. Furthermore, the invention relates to a method for making an intraocular lens. Moreover, the invention also relates to a method for implanting an intraocular lens into an eye, in which the intraocular lens is introduced into the capsular bag through an opening in the capsular bag of the eye.

BACKGROUND OF THE INVENTION

It is known that the natural lens in a human or animal eye can be removed, in particular by phacoemulsification, and replaced by an artificial intraocular lens (IOL). The inserted or implanted intraocular lens must however be attached very precisely in a site-specific manner in order to achieve the desired optical imaging properties and be able to compensate the visual defect of the eye to be corrected in the best possible manner. Here, very different embodiments of intraocular lenses are known. They usually have an optical part and, adjoining thereon, one or more haptic parts. Using these haptic parts or the haptic, the intraocular lens is stabilized in the capsular bag of the eye in terms of position.

During such eye surgery, the anterior capsular bag is cut open, the natural lens core is removed after comminution and the artificial intraocular lens is injected through the cornea via an injector. Since intraocular lenses are made of materials that have a higher refractive power than the human eye tissue, they are very thin compared to the natural lens. Therefore, the aforementioned haptic parts are provided for stabilization purposes. These haptic parts are usually spanned at the equator of the capsular bag and allow the intraocular lens to be positioned in a manner defined in the lateral and axial direction. During the subsequent healing process, the capsular bag shrinks to the intraocular lens and finally ensures the desired long-term stability. The location of the intraocular lens after the healing process is referred to as "effective lens position". During the simultaneous treatment of cataracts and astigmatism, the ideal target axis for the toric intraocular lens, along which this toric intraocular lens is aligned during surgery, is calculated pre-surgery. An exact long-term alignment of the toric intraocular lens along the target axis is decisive for the success of the simultaneous astigmatism correction.

In respect of the haptic parts, it is known that these open out in a wing-like or sidepiece-like manner at opposite sides of the optical part and project therefrom.

Moreover, options for holding the intraocular lens directly by the anterior capsular bag or for inserting the intraocular lens into the anterior chamber of the eye are also known.

In currently known intraocular lenses, the so-called secondary cataract may occur in the implanted state. A so-called secondary cataract develops in some cases since small remains of the natural lens core often remain in the capsular bag during cataract surgery and these remains are in direct contact with the nutrient liquid of the anterior eye segment. The latter leads to new optical opacification and must therefore likewise be removed or treated. Moreover, the alignment of toric intraocular lenses is already subject to a certain susceptibility to errors during the insertion. The alignment of the toric intraocular lens undertaken by the surgeon during the operation often does not correspond exactly to the calculated ideal alignment. Moreover, the shrinking process of the capsular bag during healing after a cataract operation is subject to natural variations. By way of example, if the capsular bag was not cut open in an exactly circular manner during the operation or if the intraocular lens is not placed concentrically in relation to the capsular bag opening, the final position of the intraocular lens may shift, which is referred to as post-rotation. Since the effective lens position does not correspond to the lens position established in advance, the visual acuity of the patient deteriorates in these embodiments. There is then a significant loss of vision in the case of, in particular, toric and multi-focal high-quality intraocular lenses in these embodiments. This inserted intraocular lens may even have to be removed by surgery again in this case.

Moreover, it should be mentioned that the haptic parts merely serve to stabilize the intraocular lens and therefore represent increased material expenditure which, from a clinical point of view, would not be required in the case of modified intraocular lens stabilization.

SUMMARY OF THE INVENTION

It is an object of the invention to provide an intraocular lens and a method for making such an intraocular lens which render it possible to permanently improve the positional arrangement of an intraocular lens in an eye. It is also an object of the present invention to provide a method for implanting an intraocular lens into an eye, via which the position of the introduced lens can be maintained exactly and permanently.

An intraocular lens according to the invention includes an optical part and a haptic adjoining the optical part and connected therewith. An essential concept of the invention should be seen in that at least one additional fixation element that differs from the haptic is formed on at least an upper side of the intraocular lens, which additional fixation element is formed to fix the position of the intraocular lens during insertion into a capsular bag of an eye. Thus, via the at least one additional fixation element, a concrete element is formed at the intraocular lens itself, which element then improves, particularly also in a functional and spatially-defined manner, the positioning of the whole intraocular lens in a capsular bag of an eye in the inserted state and enables a permanent fixation of the position of the inserted intraocular lens.

Therefore, a connection element affixing the intraocular lens is consequently formed on the lens itself, which connection element forms a defined fixing connection with the capsular bag of the eye. The fixation element is therefore a lens-fixing capsular bag connection element.

Preferably, provision is made for a plurality of fixation elements to be formed on the intraocular lens, wherein these, in particular, are respectively embodied as elevations. The fixation of the position can be further improved by this geometric forming and by virtue of a plurality of individual separate fixation elements also being formed at the intraocular lens and, in particular, being present in addition to the haptics.

Preferably, provision is made for at least one of the elevations to be formed as a dome or knob or bump. This specific geometry is therefore, in particular, provided with a corner-free contour such that the positioning in the capsular bag of the eye is particularly advantageous. The interaction and, in particular, the interlocking and therefore exact-fit abutment against a complementary, mechanically interacting region of the capsular bag can be achieved particularly advantageously as a result of this geometric embodiment. It particularly advantageously brings about the permanent fixation of the position. Moreover, there is no unwanted disturbing friction due to edges or corners, and so the comfort of wear in the implanted state is also particularly high for the patient.

Provision can be made for these pluralities of elevations to have the same form in terms of shaping and/or dimensions. However, provision can also be made for at least two elevations to be different in terms of shaping and/or dimensions.

In a further embodiment, provision can additionally or alternatively be made for at least one elevation to be formed as a ring at least partly extending around the main optical axis of the intraocular lens. In particular, this embodiment is configured in such a way that the ring has a circumferentially closed configuration. As a result of such rotational symmetry, a particularly advantageous fixation of the position at, or relative to, the capsular bag can also be achieved. Moreover, relatively equal mechanical contact forces occur here between the elevation and the capsular bag in the circumferential direction around the main optical axis.

Provision can also be made for at least two elevations as separate and closed rings which are radially spaced apart around the main optical axis in the circumferential direction to be formed as fixation elements.

Advantageously, provision is made for the at least one fixation element to be formed integrally with the intraocular lens. As a result, it is arranged at the intraocular lens in a positionally secured manner. Consequently, it cannot be lost and can therefore also be formed at defined and desired local positions of the intraocular lens and kept there. Moreover, it is also simpler to produce by such an embodiment from a manufacturing point of view and the intraocular lens can be produced quicker and precisely in view of the overall shaping thereof.

Preferably, provision is made for at least one fixation element to be formed on at least an upper side of the haptic. Consequently, an additional fixation element is not superimposed on the optical part in such an embodiment. In the case of specific intraocular lenses, this can be advantageous to the extent that the optical imaging property of the optical part is not disadvantageously impaired thereby.

Preferably, the fixation elements are only formed on at least an upper side of the haptic, particularly if they are embodied as elevations in the form of domes.

Preferably, provision is made for the at least one fixation element, in particular for a plurality of fixation elements, to be formed on that upper side of one or more optical parts which, in the inserted state of the intraocular lens in the capsular bag, faces or face away from the cornea of the eye. This is advantageous to the extent that, in the counter elements in the capsular bag advantageously still to be produced then already in the implanted state of the intraocular lens, the positioning precision in this respect of the embodiment of the counter elements is improved.

Additionally, or instead of this, there can also be formed at least one fixation element on the other upper side of the haptic and then consequently be present on the anterior side.

The at least one elevation can be marked in color. It can also be formed from a fluorescing material. As a result of these specifications, they can be precisely localized when the lens is introduced into the capsular bag.

Preferably, in a further embodiment, provision can be made for at least one fixation element to be formed on at least an upper side of the optical part. This can be provided in addition, or instead of, the aforementioned optional embodiment. In particular, this is advantageous if the fixation element is only generated in its final embodiment by a subsequent action of energy in the state where it is already inserted into the capsular bag. In this context, particularly the accessibility and the processability with a processing tool, in particular a laser, can be simpler at the optical part than at a haptic part in specific intraocular lenses, for example if the haptic parts are only thin curved side pieces.

Preferably, provision is made for a dye to be integrated into the material of the intraocular lens at at least one locally defined point of the optical part and/or the haptic, which dye is formed dependent on an energy influx for the purposes of defined generation of the fixation element. Thus, in such an embodiment, a material, namely a dye, which is different from the usually present polymer material of the intraocular lens, is formed in a locally delimited manner. Then, as it were, a functionally unfinished state and/or an unfinished state in terms of form or a basic state of the fixation element is also prescribed in an integrated manner as a result of this difference of material and the at least one locally defined point, at which the dye is present. Consequently, as it were, a fixation element is also already, to a certain extent, formed in the intraocular lens in these embodiments but still provided in a virtually unfinished state. In particular, the finished state of the fixation element is then only achieved by virtue of this dye subsequently being processed by an energy influx, in particular by laser light, and, as a result of this, a connecting interaction with the capsular bag occurring such that a fixation of the position with the capsular bag then occurs in this case.

The dye can be embedded in the polymer material at the defined points or it can be applied as a layer onto the surface of the polymer material. The dye is preferably trypan blue or methylene blue. However, a different biocompatible dye can also be provided.

The dye is preferably formed in a chemically encapsulated form. As a result, biocompatibility is ensured if cytotoxicity should occur.

The dye is preferably selected in such a way that it maximally absorbs the laser light provided during the fixation in the capsular bag. The thermal energy which is preferred during the specific fixation in the form of fusion with the capsular bag is generated in that case in particular.

In the optical part thereof, the lens can be formed as a rotationally symmetrical lens; however, it can also be formed as a toric intraocular lens.

Moreover, the invention relates to a method for producing an intraocular lens, which is formed with an optical part and a haptic adjoining the optical part. At least one fixation element is formed on at least an upper side of the intraocular lens, which fixation element is functionally formed for fixing the position of the intraocular lens in the capsular bag of an eye.

At least one basic state of the fixation element is already formed during the production of the intraocular lens and it is therefore generated prior to further use and consequently also, in particular, prior to the produced intraocular lens being implanted in a capsular bag.

In particular, one, preferably all, fixation elements are already completely formed during the manufacturing of the intraocular lens and consequently completed in the final state of a fixation element.

Provision can also be made for a fixation element to be formed in a form-specifically and/or effect-specifically occurring intermediate state during the production of the intraocular lens, in particular integrated therein. The intraocular lens then produced in this respect can then be completed or provided with its final form in respect of the final embodiment of the fixation element when implanting the intraocular lens into the capsular bag of the eye. This is possible, in particular, in an embodiment in which a dye is introduced into, or attached to, a locally defined point of the intraocular lens, in particular the optical part of the intraocular lens, during the production of the intraocular lens. Once the lens has been completed, this dye can then subsequently be processed further when the intraocular lens is introduced into the capsular bag. In particular, this can be carried out to the extent that an energy influx, for example or preferably via laser light, acts on this local point with the dye in the state where the intraocular lens has already been inserted into the capsular bag and, as a result of this energy influx, the dye changes to the extent that it is connected in a mechanically stable fashion, in particular coagulated, to the material of the capsular bag by heating.

The invention also relates to a method for implanting an intraocular lens into an eye, in which the intraocular lens is introduced into the capsular bag through an opening in the capsular bag of the eye. An essential concept of the invention consists of, in addition to fastening with the intraocular lens in the eye via a haptic of the intraocular lens, the intraocular lens being connected to the capsular bag by at least one fixation element and a position of the intraocular lens in relation to the capsular bag being fixed by the fixation element. Thus, in addition to the mechanical stabilization of the intraocular lens in the eye, which is achieved by the haptic, fixing of the position of the intraocular lens in the capsular bag relative to the capsular bag is achieved via at least one further fixation element which is different from haptic parts. As a result of such a procedure, the malpositions, as specified at the outset, of the intraocular lens when it is implanted in a capsular bag of the eye can be lifted. In particular, the secondary cataract explained at the outset can be prevented thereby. After the operation, unwanted changes in the position of the intraocular lens in the capsular bag in the inserted state can also be prevented thereby during the healing process. A permanent and reliable positional arrangement of the intraocular lens can be achieved by virtue of, as it were, not only a stabilization of the intraocular lens in the capsular bag being fulfilled by the haptic, but also by an actual position fixation between the intraocular lens and the capsular bag being formed as a direct mechanical connection between the intraocular lens and the capsular bag via the at least one fixation element.

Preferably, the fixation element is formed as an elevation on an upper side of the intraocular lens prior to the insertion of the intraocular lens into the capsular bag, and a laser is used in the state of the intraocular lens where it is inserted into the capsular bag to generate at least one depression at the inner side of the capsular bag, into which depression the elevation then extends for fixing the position. As a result of this mechanical coupling in the form of an elevation/depression operating principle, very simple but nevertheless mechanically highly functional fixing of the position is enabled. An action on the material of the intraocular lens is not required in this embodiment.

Preferably, the elevation is formed in a dome-like manner and the depression is generated for the interlocking and therefore precise fit of the elevation. This is particularly advantageous since such a precise fit between the depression and the elevation brings to bear the fixing of the position to a particular extent and prevents unwanted relative movement between the intraocular lens and the capsular bag.

If the intraocular lens is introduced into the capsular bag, the exact position of the at least one fixation element is preferably detected. By way of example, this can be brought about to the extent that a fixation element which is specified in terms of color in relation to the remainder of the lens is identified. Provision can also be made for this position of the fixation element to be determined via fluorescence measurement if the fixation element is made from a fluorescent material. Provision can also be made for the position of the fixation element to be determined by an optical coherence tomography.

In an alternative embodiment, the capsular bag is fused to the intraocular lens via the action of a laser light after the intraocular lens is inserted into the capsular bag. Thus, compared to the aforementioned alternative embodiment, no nondestructive detachable mechanical connection is provided here, but rather a nondestructive non-detachable connection is provided. Here, fixing the position is likewise made possible in a permanently stable manner.

Preferably, the fusion connection is generated with at least one ring extending around the main optical axis of the intraocular lens, which ring, in particular, is generated on the optical part of the intraocular lens. This is a particularly advantageous embodiment. This is because a completely surrounding closed ring generates, as it were, a type of closed chamber between the intraocular lens and the capsular bag, into which no unwanted other parts, such as possible remainders of the comminuted natural lens, which were not yet removed from the capsular bag, or grown epithelial cells can then enter. The problems explained in this respect at the outset can then be prevented to a particular extent, precisely in such an embodiment. Moreover, such a rotationally symmetric fused connection extending around the main optical axis also provides a uniform connection in all radial directions, which acts not only locally and therefore leads not only locally to specific and mechanical tensions or tensile forces. As a result of the aforementioned advantageous embodiments, these mechanical influences are distributed very homogeneously such that, in this case too, the best possible fit between the capsular bag and the intraocular lens is achieved.

In order to generate the local fixation connection between the capsular bag and the intraocular lens, laser light is preferably used to irradiate a dye integrated at defined local points of the intraocular lens and at least the dye is heated by the thermal energy influx of the laser light and fused to the capsular bag by virtue of only coagulation taking place between the dye and the biological material of the capsular bag. This embodiment is also particularly advantageous as fused connections can be generated particularly precisely and locally, precisely by the thermal load on the dye, and these can be generated in a mechanically very stable and permanent manner. Moreover, no cutting of the capsular bag, only coagulation, is performed by the laser light. As a result, no unwanted connection beads form, and so the imaging properties of the lens are also not undesirably impaired, even if these fused connections are generated between the optical part of the lens and the capsular bag.

Such a fused connection can be generated on the optical part of the lens and/or on at least one haptic part, preferably near or adjoining the optical part, of the lens.

Advantageously, the lens is fixed to the capsular bag during a time-offset further surgical intervention at a later time after the surgical intervention for implanting the lens into the capsular bag has been completed. Thus, for example, the fixation can then be brought about in a further intervention a couple of hours or a day after the introduction of the lens into the capsular bag is complete. As a result, there can be particularly precise positioning.

Provision can be made for the laser light to be produced in a pulsed fashion or in continuous wave operation. Here, laser light with a wavelength of between 585 nm and 635 nm is preferably provided such that, in this case, laser light in the yellow spectral range is advantageous. Precisely this wavelength of the laser light renders possible a very precise and local treatment of the capsular bag material and/or of the lens material, and so no unwanted effects and side effects occur at the points of the capsular bag and/or of the intraocular lens. Moreover, the best possible energy influx, in particular into the specific dye, more particularly trypan blue or methylene blue, is achieved with precisely this laser light such that the processes for heating this dye by exciting the dye by the laser light and the subsequently cohesive, and therefore permanent, secure connection with the material of the capsular bag by material-mixing are brought about particularly advantageously. The precise position of the dye can be identified by for example color difference from the remainder of the material or by fluorescence measurement in this embodiment as well.

Provision can also be made for the capsulotomy to be adapted in its form. Here, for a specific intraocular lens, it is not only the diameter of the capsulotomy that is adapted thereto, but also the form. For toric intraocular lenses, provision can be made for a rotation in the capsular bag to be counteracted by the form of the capsulotomy. Since a rotation can already be caused by relatively small forces, a weak force component could be sufficient to prevent the toric intraocular lens from rotating or even to rotate this toric intraocular lens into the correct location. By way of example, this is achieved by an elliptic form of the capsulotomy. A capsulotomy adapted to the specific embodiment of the intraocular lens is preferably calculated from pre-operative data, in particular including data of the intraocular lens and the eye to be operated on, and it is provided as base information to a laser for cutting purposes. In particular, a corresponding ideal alignment of the patient in relation to the surgical microscope and consequently, in particular, in relation to the laser as well should be set in this case. By way of example, this could be implemented by tracking via an operating system such that the axis of the alignment of the elliptic capsulotomy fits the planned axis of the toric intraocular lens.

Using the invention, the intraocular lens can, in general, also be securely anchored to the capsular bag, postoperatively either through the embodiment of knob-like elevations or by the generation of fused connections, in particular in the form of rings. As a result, it is also possible to determine whether the operation has restored the desired visual acuity and, subsequently, fix the intraocular lens in its final position, wherein this can be the case via the aforementioned options. In particular, the invention at least substantially reduces the above-described secondary cataract to a great extent, also by virtue of lens epithelial cells no longer being able to grow in an unhindered manner along the specially prepared intraocular lens.

BRIEF DESCRIPTION OF THE DRAWINGS

The invention will now be described with reference to the drawings wherein.

DESCRIPTION OF THE PREFERRED
EMBODIMENTS OF THE INVENTION

In FIGS. 1 to 5C, the same or functionally equivalent elements are provided with the same reference signs.

Figure 1:
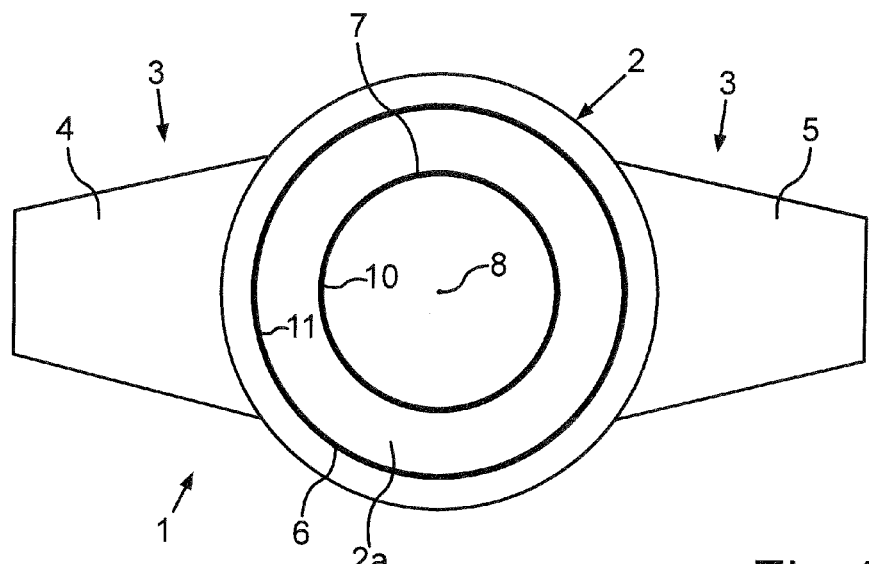
FIG. 1 shows a plan view of an embodiment of an intraocular lens according to the invention.

FIG. 1 is a schematic of an intraocular lens 1 having an optical part 2 and a haptic 3 with haptic parts 4 and 5. In terms of their form as plate-like wings, the haptic parts 4 and 5 should likewise be understood merely in an exemplary manner and they adjoin the edge of the optical part 2 and are integrally formed on opposite sides of the optical part 2. The haptic parts 4 and 5 could also be formed as strand-like, thin and bent side pieces.

Provision is made in the embodiment for fixation elements 6 and 7 to be configured on an upper side 2a of the optical part 2. In the embodiment shown in FIG. 1, these fixation elements 6 and 7 are formed as closed rings, which extend around a main axis 8, which is perpendicular to the plane of the figures, of the optical part 2 in a rotationally symmetric manner. These fixation elements (6, 7) can be elevations integrated into the optical part 2. The intraocular lens 1 is fixed in terms of position in a capsular bag 9 (FIG. 2) of an eye via these fixation elements. Consequently, in addition to the stabilization of the intraocular lens 1 in the capsular bag 9, which, in particular, is obtained by the haptic parts 4 and 5, the position is also fixed by the fixation elements 6 and 7.

In particular, when the intraocular lens 1 is implanted in the capsular bag 9, it is arranged in such a way that the upper side 2a is the posterior side, which is therefore arranged facing away from a cornea of the eye.

In addition to, or instead of, the fixation elements 6 and 7, provision can also be made for at least one fixation element to be formed integrally on an upper side of the haptic part 4 and/or for at least one fixation element to be formed integrally on an upper side of the haptic part 5.

In an advantageous embodiment, provision is made for a specific dye (10, 11) to be formed integrated locally into the material of the optical part 2, which, in particular, is a polymer material, at those points at which the rings, as fixation elements 6 and 7, are intended to be formed. Here, provision can be made for the dye (10, 11) to be embedded into the polymer material or to be applied as a layer on the surface of the polymer material. In such embodiments, the final embodiment of the fixation elements 6 and 7 is not yet provided in this case, but a functional, form-type and localized base state of these fixation elements (6, 7) is already prescribed by the concrete dye present.

If the intraocular lens 1 provided in this respect is then introduced into the capsular bag 9 during a surgical procedure, the final embodiment of the fixation elements 6 and 7 is formed via a laser light, particularly in the yellow spectral range. To this end, the laser light is directed, in particular focused, in a targeted fashion onto those local points on the upper side 2a at which the dye 10 or 11 has been introduced. As a result of the energy influx of the laser light into these local positions, the dye is heated and fused to the capsular bag 9 by virtue of the dye (10, 11) being coagulated with the capsular bag 9. Thus, no cutting of the materials is required here as a result of the laser, which is advantageous for the capsular bag 9 and healing. Then, a cohesive and non-destructive non-detachable mechanical connection is formed between the intraocular lens 1 and the capsular bag 9.

Figure 2:
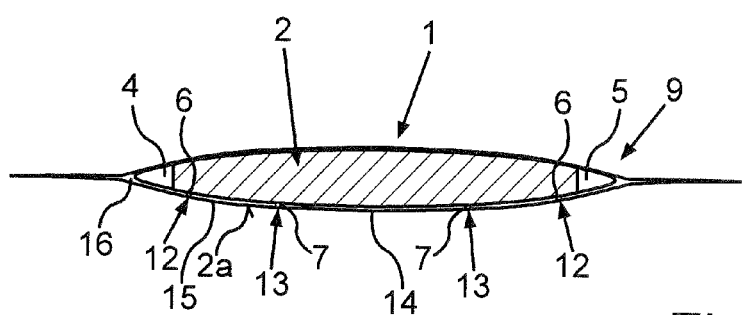
FIG. 2 is a section view of an intraocular lens of FIG. 1, implanted in a capsular bag of an eye.

In the section view of FIG. 2, the intraocular lens 1, as was explained in FIG. 1 using the example with fused connections (12, 13) on the optical part 2, is shown in the fixed-position final location in the capsular bag 9. Here, the fused connections (12, 13) are shown highlighted in a symbolically thickened manner. In actual fact, there are virtually no elevations or thickenings and the optical part 2 abuts directly on an inner side 9a of the capsular bag 9.

Then, as a result of the closed rings and the fused connections 12 and 13, sealed chambers 14 and 15 are consequently formed between the capsular bag 9 and the intraocular lens 1 in this embodiment. This prevents residual particles of the comminuted natural lens from being able to enter into these chambers 14 and 15 and, moreover, lens epithelial cells 16, which may occur at the edges of the capsular bag 9 after the implantation, are also prevented from being able to enter the chambers 14 and 15.

Such an intraocular lens 1 is then implanted to the extent that it is initially produced and provided as explained above and the capsular bag 9 is then opened during an operation and this intraocular lens 1 is inserted. If the predetermined and desired location of the intraocular lens 1 in the capsular bag 9 is then formed and determined, in particular within the scope of a further step, the position is fixed in the aftermath by the action of the laser light, wherein this is then carried out, for example and in particular, by the intraocular lens 1, in particular the optical part 2, being fused with the capsular bag 9 at the local points.

The position is preferably only fixed after a completed implantation operation in a separate, time-offset further surgical procedure, for example approximately one day after the implantation of the intraocular lens 1.

Figure 3:
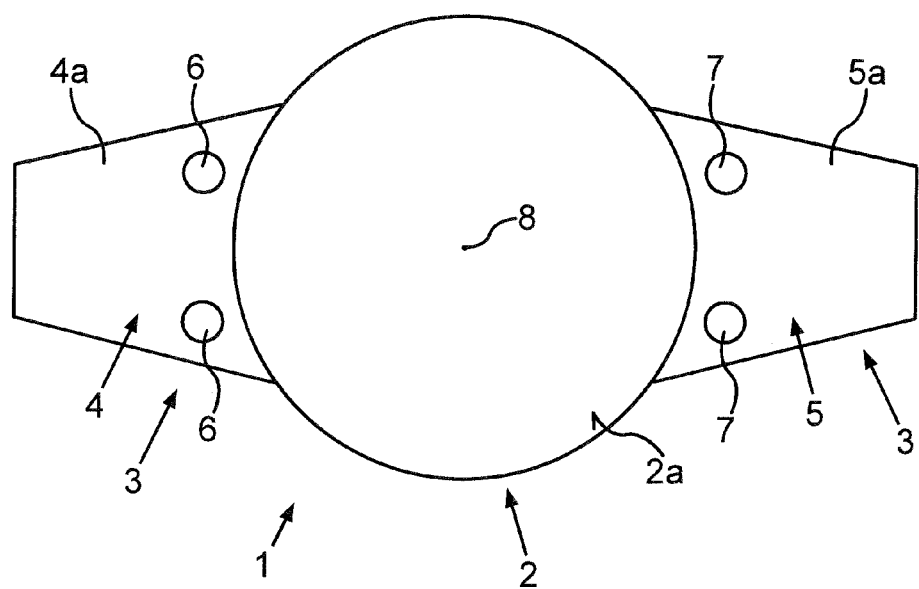
FIG. 3 shows a plan view of a further embodiment of an intraocular lens according to the invention.

FIG. 3 shows a further embodiment of an intraocular lens 1. In this embodiment, provision is preferably made for in each case a plurality of fixation elements 6 and 7 to be formed in an integrated manner, at least on a posterior upper side 4a and/or 5a. In particular, these dome-like or bump-like or knob-like elevations are integrated into the haptic parts 4 and/or 5 and formed from the same material. Attention is drawn to the fact that both the number and the local position of these fixation elements 6 and 7 in FIG. 2 should merely be understood in an exemplary manner. Provision can also be made for, additionally, at least one fixation element to be formed on an upper side, in particular the upper side 2a of the optical part.

Figure 4A:
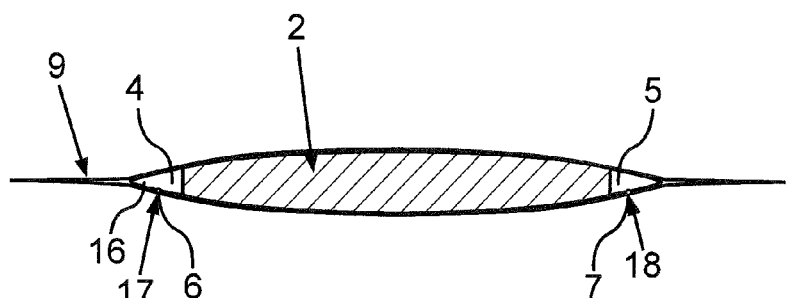
FIGS. 4A and 4B are section views in which an intraocular lens in accordance with FIG. 3 is implanted in a capsular bag of the eye; and, FIGS. 5A to 5C are respective schematics of toric intraocular lenses with elliptic form of the capsulotomy.
Figure 4B:
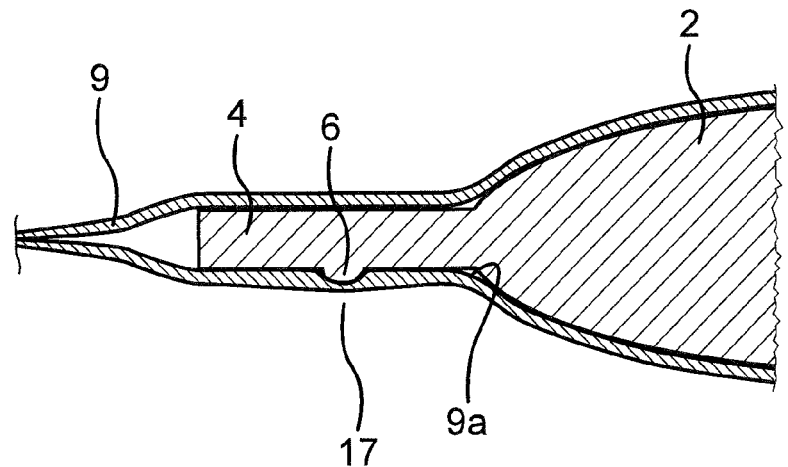

FIGS. 4A and 4B then, in turn, show the state of the intraocular lens 1 when implanted into the capsular bag 9. Here too, the intraocular lens 1 is fixed in position in the capsular bag 9. Here, the fixation elements 6 and 7 abut directly against an inner side of the capsular bag 9. They are arranged in an engaging manner, in particular in an interlocking manner and therefore with precise fit in depressions 17 and 18, which are generated on an inner side 9a of the capsular bag 9 in a targeted and defined manner by the action of a treatment tool, in particular a laser. Thus, in particular, an interlocking fit is generated between the fixation elements 6 and 7 and the depressions 17 and 18 in this case. Here too, fixing is achieved, in particular via laser light after the introduction of the intraocular lens 1 into the eye and after the correct alignment and positioning. To this end, the inner side 9a is treated by laser light in such a way that the depressions 17 and 18 are generated, in particular at those points at which the fixation elements 6 and 7 abut against the capsular bag 9 or this inner side 9a. Then, no cohesive and, consequently, no material-mixing connection is formed in this embodiment, but rather an interlocking mechanical connection between the depressions 17 and 18 and the fixation elements 6 and 7. These depressions 17 and 18 are burnt into the inner side 9a via the laser light. To this end, a laser can also be used in either pulsed operation or in continuous wave operation in this case.

The intraocular lenses 1 can be embodied in a rotationally symmetric manner or else be embodied as toric lenses.

Figures 5A, 5B, 5C:
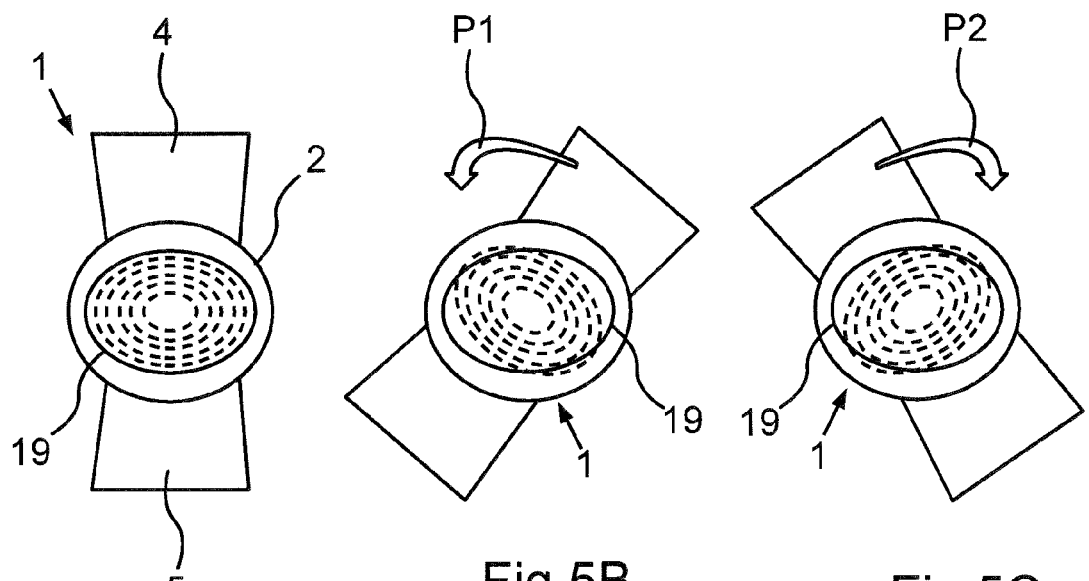

FIGS. 5A to 5C show, in schematics, examples of toric intraocular lenses 1, in which, additionally to the stabilization of the intraocular lens 1 in the capsular bag by the haptic parts 4 and 5, the position is fixed by a specifically adapted capsulotomy. This is done to the effect that the capsulotomy with the elliptic form 19 thereof is generated with a precise location and, as it were, adapted to the non-rotationally-symmetric form of the toric lens 1. What this achieves in accordance with the illustrations in FIGS. 5A to 5C is that the intraocular lenses 1 can likewise be arranged with a fixed position in the capsular bag. The positionally fixed state in this respect is shown in the left-hand illustration of FIG. 5A. If the lens is positioned differently, it is possible to identify, for example in the central illustration of FIG. 5B, that the rotational movement of the intraocular lens 1, indicated by the arrow P1, as it were forces the latter into the correct position. A corresponding state is shown in the right-hand illustration of FIG. 5C, in which the intraocular lens 1 is forced in terms of its movement in the direction of the arrow P2, in order then, once again, likewise to assume the precise fit with respect to the elliptic form of the capsulotomy and, in this respect, as it were also to "latch in" accordingly. In particular, the axes of the alignment of the elliptic capsulotomy and of the toric intraocular lens 1 are then arranged in a fitting-together or coincident manner.

It is understood that the foregoing description is that of the preferred embodiments of the invention and that various changes and modifications may be made thereto without departing from the spirit and scope of the invention as defined in the appended claims.

What is claimed is:

1. A method for implanting an intraocular lens into an eye, the intraocular lens including an optical part and a haptic, the method comprising the steps of:
   inserting the intraocular lens into a capsular bag of the eye through an opening in the capsular bag;
   fastening the intraocular lens in the capsular bag via the haptic;
   connecting the intraocular lens to the capsular bag via at least one fixation element while fixing the position of the intraocular lens in the capsular bag with said fixation element; and,
   fusing the capsular bag with the intraocular lens in a coagulating manner via a laser to form a fused connection after the intraocular lens has been inserted into the capsular bag.

2. The method of claim 1, wherein the intraocular lens defines an optical axis and the fused connection is generated with at least one annulus extending around the optical axis.

3. The method of claim 2, wherein the haptic has a first haptic part and a second haptic part; and, the annulus is generated on at least one of the first haptic part, the second haptic part and the optical part.

4. The method of claim 1, wherein a dye is integrated into a defined location of the intraocular lens, the method further comprising the step of:
  irradiating the dye at the defined location of the intraocular lens via laser light for generating a local fixation connection between the capsular bag and the intraocular lens and fusing the dye with the capsular bag in a coagulating manner via the thermal energy influx of the laser light.

5. The method of claim 4, wherein the laser light lies in a yellow wavelength range.

6. The method of claim 4, wherein the dye is one of trypan blue and methylene blue.

* * * * *